(12) United States Patent
Brin et al.

(10) Patent No.: US 6,974,579 B2
(45) Date of Patent: Dec. 13, 2005

(54) METHODS FOR TREATING VASCULAR DISORDERS

(75) Inventors: Mitchell F. Brin, Newport Beach, CA (US); Markus K. Naumann, Kurnach (DE)

(73) Assignee: Allergan, Inc., Irvine, CA (US)

(*) Notice: Subject to any disclaimer, the term of this patent is extended or adjusted under 35 U.S.C. 154(b) by 0 days.

(21) Appl. No.: 10/754,364

(22) Filed: Jan. 8, 2004

(65) Prior Publication Data

US 2005/0152923 A1 Jul. 14, 2005

(51) Int. Cl.$^7$ .................. A61K 39/08; A61K 39/02; A61K 39/00
(52) U.S. Cl. .................. 424/239.1; 424/236.1; 424/234.1; 424/184.1; 424/247.1
(58) Field of Search ............... 424/239.1, 184.1, 424/236.1, 234.1, 247.1; 514/2

(56) References Cited

U.S. PATENT DOCUMENTS

| | | | |
|---|---|---|---|
| 5,376,376 A | * | 12/1994 | Li ........................ 424/443 |
| 5,437,291 A | | 8/1995 | Pasricha et al. |
| 5,670,484 A | | 9/1997 | Binder |
| 5,714,468 A | | 2/1998 | Binder |
| 5,766,605 A | | 6/1998 | Sanders et al. |
| 5,989,545 A | | 11/1999 | Foster et al. |
| 6,063,768 A | | 5/2000 | First |
| 6,139,845 A | | 10/2000 | Donovan |
| 6,265,379 B1 | | 7/2001 | Donovan |
| 6,299,893 B1 | | 10/2001 | Schwartz et al. |
| 6,306,423 B1 | | 10/2001 | Donovan et al. |
| 6,312,708 B1 | | 11/2001 | Donovan |
| 6,358,926 B2 | | 3/2002 | Donovan |
| 6,423,319 B1 | | 7/2002 | Brooks et al. |
| 6,458,365 B1 | | 10/2002 | Aoki et al. |
| 6,464,986 B1 | | 10/2002 | Aoki et al. |
| 6,579,847 B1 | * | 6/2003 | Unger ........................ 514/2 |
| 6,767,544 B2 | * | 7/2004 | Brooks et al. ............ 424/247.1 |

FOREIGN PATENT DOCUMENTS

| WO | WO 01/10458 | 2/2001 |
|---|---|---|
| WO | WO 03/084567 | 10/2003 |

OTHER PUBLICATIONS

Costello RB et al., eds. Webster's College Dictionary, 1991, Random House Inc. p. 579.*
U.S. Appl. No. 09/371,354, filed Aug. 10, 1999, Stephen Donovan.
U.S. Appl. No. 10/114,740, filed Apr. 1, 2002, Greg Brooks.
U.S. Appl. No. 10/194,805, filed Jul. 11, 2002, Stephen Donovan.
Bigalke H., et al., *Botulinum A Neurotoxin Inhibits Non-Cholinergic Synaptic Transmission in Mouse Spinal Cord Neurons in Culture*, Brain Research 360;318-324:1985.
Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316; 244-251;1981.
Binz T. et al., *The Complete Sequence of Botulinum Neurotoxin Type A and Comparison with Other Clostridial Neurotoxins*, J Biological Chemistry 265(16);9153-9158: 1990.
Bushara K., *Botulinum toxin and rhinorrhea*, Otolaryngol Head Neck Surg 1996;114(3):507.
Duggan et al., *A Survey of Botulinum neurotoxin substrate expression in cells; Mov Disord*, 10(3):376:1995.
Gonelle-Gispert et al., *Snap-25a and -25b isoforms are both expressed in insulin-secreting cells and can function in insulin secretion; Biochem J 1*, 339 (pt 1):159-65:1999.
Habermann E., et al., *Tetanus Toxin and Botulinum A and C Neurotoxins Inhibit Noradrenaline Release From Cultured Mouse Brain*, J Neurochem 51(2);522-527:1988.
Habermann E., *Inhibition by Tetanus and Botulinum A Toxin of the release of [3H]Noradrenaline and [3H]GABA From Rat Brain Homogenate*, Experientia 44;224-226:1988.
*Harrison's Principles of Internal Medicine* (1998), edited by Anthony Fauci et al., 14th edition, published by McGraw Hill.
Jankovic J. et al., *Therapy With Botulinum Toxin*, Marcel Dekker, Inc., (1994), p. 5, 150.
Moro E., et al, *Suppression of syncopes after botulinum toxin treatment*, Mov Disord 2002;17(Suppl 5):S242 ABS P780.
Moyer E et al., *Botulinum Toxin Type B: Experimental and Clinical Experience*, being chapter 6, pp. 71-85 of "Therapy With Botulinum Toxin", edited by Jankovic, J. et al. (1994), Marcel Dekker, Inc.
Naumann et al., *Botulinum toxin type A in the treatment of focal, axillary and palmar hyperhidrosis and other hyperhidrotic conditions*; European J. Neurology 6 (Supp 4): S111-S1150:1999.
Pearce, L.B., *Pharmacologic Characterization of Botulinum Toxin For Basic Science and Medicine*, Toxicon 35(9);1373-1412 at 1393.
Ragona et al., *Management of Parotid Sialocele with Botulinum Toxin; The Laryngoscope* 109:1344-1346:1999.
Sanchez-Prieto, J., et al., *Botulinum Toxin A Blocks Glutamate Exocytosis From Guinea Pig Cerebral Cortical Synaptosomes*, Eur J. Biochem 165;675-681:1897.

(Continued)

Primary Examiner—Sandra E. Saucier
Assistant Examiner—Lora E Barnhart
(74) Attorney, Agent, or Firm—Stephen Donovan

(57) ABSTRACT

The present invention provides methods for improving blood supply through a grafted blood vessel. In some embodiments, the methods comprise the step of locally administering a botulinum toxin to the grafted blood vessel, thereby improving blood supply through the grafted blood vessel.

7 Claims, No Drawings

OTHER PUBLICATIONS

Sterodimas, A., et al., *Successful use of botulinum toxin-A for the treatment of neck and anterior chest wall flushing*, Clinical and Experimental Dermatology, 2003 Blackwell Publishing Ltd., vol. 28, p. 592-594.

Schantz, E.J., et al, *Properties and use of Botulinum toxin and Other Microbial Neurotoxins in Medicine*, Microbiol Rev. 56;80-99:1992.

Singh, *Critical Aspects of Bacterial Protein Toxins*, pp. 63-84 (chapter 4) of Natural Toxins II, edited by B.R. Singh et al., Plenum Press, New York (1976).

Sloop et al., *Reconstituted Botulinum toxin type A does not lose potency in humans if it is refrozen or refrigerated for 2 weeks before use*; Neurology, 48:249-53:1997.

Tugnoli V., et al., *The role of gustatory flushing in Frey's syndrome and its treatment with botulinum toxin type A*, Clin Auton Res 2002;12(3):174-178.

Kellogg, Jr., Dean L., et al., *Cutaneous Active Vasodilation in Humans is Mediated by Cholinergic Nerve Cotransmission*, vol. 77(6), Dec. 1995, American Heart Association, Inc., Lippincott Williams & Wilkins, pp. 1222-1228.

* cited by examiner

METHODS FOR TREATING VASCULAR DISORDERS

BACKGROUND

The present invention relates to methods for treating vascular disorders. In particular the present invention relates to methods for treating vascular disorders with a botulinum toxin.

A vascular disorder can include a vasomotor instability condition, which is a condition associated with, or caused by, abnormal tone or abnormal constriction or dilation of a blood vessel. Thus, a vasomotor instability condition can include an excessive dilatation, an excessive contraction, or abnormality in the contraction-relaxation process of a blood vessel, including in a region or complex of blood vessels. A vasomotor instability condition is normally regulated by elements in the blood vessel wall and/or by attendant innervation. A blood vessel includes an artery, vein, and capillary and any similar structure which carries blood in the body of a mammal.

An indicated a vasomotor instability condition can be characterized by an excessive blood vessel contraction. The afflicted blood vessel can be located in the periphery, within an organ, on top of an organ, feeding an organ, including the brain and in any other tissue of the body.

Vasomotor instability can include conditions such as Raynaud's syndrome, an arterial-venous malformation, atherosclerosis, pulmonary hypertension, or can result from a blood vessel graft or from a kidney transplant. Raynaud's syndrome is characterized by a pale-blue-red sequence of color changes of the digits, most commonly after exposure to cold. Raynaud's syndrome occurs associated with spasm of a blood vessel. An arterial-venous malformation can involve just the arterial or the venous circulation or both. Atherosclerosis is a disease of the large arteries and the primary cause of heart disease and stroke. Apparently, atherosclerosis is not simply an inevitable degenerative consequence of ageing, but is rather a chronic inflammatory condition that can be converted into an acute clinical event by plaque rupture and thrombosis.

In pulmonary hypertension the vascular lumen is reduced because of proliferation of endothelial cells forming plexiform or concentric lesions, myofibroblasts embedded in a mucopolysaccharide matrix, and media vascular thickening. Excessive vasoconstriction has been the prevailing hypothesis of the pathobiology of pulmonary hypertension and several studies have investigated whether a deficiency of vasodilators such as prostacyclin is present in patients.

Kidney Transplantation is the therapy of choice for nearly all patients with end-stage renal disease and is the most common type of transplant in the United States. Common post-transplant complications are toxicity due to vasoconstriction of renal arterioles and the vasoconstrictive properties may be responsible for severe bone pain and hypertension.

Botulinum Toxin

The genus *Clostridium* has more than one hundred and twenty seven species, grouped according to their morphology and functions. The anaerobic, gram positive bacterium *Clostridium botulinum* produces a potent polypeptide neurotoxin, *botulinum* toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and attack peripheral motor neurons. Symptoms of *botulinum* toxin intoxication can progress from difficulty walking, swallowing, and speaking to paralysis of the respiratory muscles and death.

*Botulinum* toxin type A is the most lethal natural biological agent known to man. About 50 picograms of a commercially available *botulinum* toxin type A (purified neurotoxin complex)[1] is a LD50 in mice (i.e. 1 unit). One unit of BOTOX® (a *botulinum* toxin type A purified neurotoxin complex, which is also referred to as a *botulinum* toxin type A complex) contains about 50 picograms (about 56 attomoles) of *botulinum* toxin type A complex. Interestingly, on a molar basis, *botulinum* toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins*, pages 63–84 (chapter 4) of Natural Toxins II, edited by B. R. Singh et al., Plenum Press, New York (1976) (where the stated LD50 of *botulinum toxin* type A of 0.3 ng equals 1 U is corrected for the fact that about 0.05 ng of BOTOX® (a *botulinum* toxin type A complex) equals 1 unit). One unit (U) of *botulinum* toxin is defined as the LD50 upon intraperitoneal injection into female Swiss Webster mice weighing 18 to 20 grams each.

[1]Available from Allergan, Inc., of Irvine, Calif. under the tradename BOTOX® in 100 unit vials)

Seven generally immunologically distinct *botulinum* neurotoxins have been characterized, these being respectively *botulinum* neurotoxin serotypes A, B, C1, D, E, F and G each of which is distinguished by neutralization with type-specific antibodies. The different serotypes of *botulinum* toxin vary in the animal species that they affect and in the severity and duration of the paralysis they evoke. For example, it has been determined that *botulinum* toxin type A is 500 times more potent, as measured by the rate of paralysis produced in the rat, than is *botulinum* toxin type B. Additionally, *botulinum* toxin type B has been determined to be non-toxic in primates at a dose of 480 U/kg which is about 12 times the primate LD50 for *botulinum* toxin type A. Moyer E et al., *Botulinum Toxin Type B: Experimental and Clinical Experience*, being chapter 6, pages 71–85 of "Therapy With Botulinum Toxin", edited by Jankovic, J. et al. (1994), Marcel Dekker, Inc. *Botulinum* toxin apparently binds with high affinity to cholinergic motor neurons, is translocated into the neuron and blocks the release of acetylcholine as well as other substances and neurotransmitters. Additional uptake can take place through low affinity receptors, as well as by phagocytosis and pinocytosis.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain, H chain, and a cell surface receptor; the receptor is thought to be different for each type of *botulinum* toxin and for tetanus toxin. The carboxyl end segment of the H chain, HC, appears to be important for targeting of the toxin to the cell surface.

In the second step, the toxin crosses the plasma membrane of the cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, HN, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of botulinum toxin activity appears to involve reduction of the disulfide bond joining the heavy chain, H chain, and the light chain, L chain. The entire toxic activity of botulinum and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Botulinum toxin serotype A and E cleave SNAP-25. Botulinum toxin serotype C1 was originally thought to cleave syntaxin, but was found to cleave both syntaxin and SNAP-25. Each of the botulinum toxins specifically cleaves a different amino acid sequence, except botulinum toxin type B (and tetanus toxin) which cleave the same amino acid sequence of the relevant docking protein. Each of these cleavages block the process of vesicle-membrane docking, thereby preventing exocytosis of vesicle content.

Botulinum toxins have been used in clinical settings for the treatment of neuromuscular disorders characterized by hyperactive skeletal muscles (i.e. motor disorders). In 1989 a botulinum toxin type A complex has been approved by the U.S. Food and Drug Administration for the treatment of blepharospasm, strabismus and hemifacial spasm. Subsequently, a botulinum toxin type A was also approved by the FDA for the treatment of cervical dystonia and for the treatment of glabellar lines, and a botulinum toxin type B was approved for the treatment of cervical dystonia. Non-type A botulinum toxin serotypes apparently have a lower potency and/or a shorter duration of activity as compared to botulinum toxin type A. Clinical effects of peripheral intramuscular botulinum toxin type A are usually seen within one week of injection. The typical duration of symptomatic relief from a single intramuscular injection of botulinum toxin type A averages about three months, although significantly longer periods of therapeutic activity have been reported.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type C1 has been shown to cleave both syntaxin and SNAP-25. These differences in mechanism of action may affect the relative potency and/or duration of action of the various botulinum toxin serotypes. Apparently, a substrate for a botulinum toxin can be found in a variety of different cell types. See e.g. Biochem J 1;339 (pt 1):159–65:1999, and Mov Disord, 10(3):376: 1995 (pancreatic islet B cells contains at least SNAP-25 and synaptobrevin).

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and C1 is apparently produced as only a 700 kD or 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of injection of a botulinum toxin complex.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine (Habermann E., et al., *Tetanus Toxin and Botulinum A and C Neurotoxins Inhibit Noradrenaline Release From Cultured Mouse Brain*, J Neurochem 51(2);522–527:1988) CGRP, substance P and glutamate (Sanchez-Prieto, J., et al., *Botulinum Toxin A Blocks Glutamate Exocytosis From Guinea Pig Cerebral Cortical Synaptosomes*, Eur J. Biochem 165;675–681:1897. Thus, when adequate concentrations are used, stimulus-evoked release of most neurotransmitters is blocked by botulinum toxin. See e.g. Pearce, L. B., *Pharmacologic Characterization of Botulinum Toxin For Basic Science and Medicine*, Toxicon 35(9);1373–1412 at 1393; Bigalke H., et al., *Botulinum A Neurotoxin Inhibits Non-Cholinergic Synaptic Transmission in Mouse Spinal Cord Neurons in Culture*, Brain Research 360;318–324:1985; Habermann E., *Inhibition by Tetanus and Botulinum A Toxin of the release of [3H]Noradrenaline and [3H]GABA From Rat Brain Homogenate*, Experientia 44;224–226:1988, Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316;244–251:1981, and; Jankovic J. et al., *Therapy With Botulinum Toxin*, Marcel Dekker, Inc., (1994), page 5.

Botulinum toxin type A can be obtained by establishing and growing cultures of Clostridium botulinum in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, *botulinum* toxin serotypes C1, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the *botulinum* toxin type B serotype only cleave a portion of the toxin produced. The exact proportion of nicked to unnicked molecules depends on the length of incubation and the temperature of the culture. Therefore, a certain percentage of any preparation of, for example, the *botulinum* toxin type B toxin is likely to be inactive, possibly accounting for the known significantly lower potency of *botulinum* toxin type B as compared to *botulinum* toxin type A. The presence of inactive *botulinum* toxin molecules in a clinical preparation will contribute to the overall protein load of the preparation, which has been linked to increased antigenicity, without contributing to its clinical efficacy. Additionally, it is known that *botulinum* toxin type B has, upon intramuscular injection, a shorter duration of activity and is also less potent than *botulinum* toxin type A at the same dose level.

High quality crystalline *botulinum* toxin type A can be produced from the Hall A strain of *Clostridium botulinum* with characteristics of $\geq 3 \times 107$ U/mg, an A260/A278 of less than 0.60 and a distinct pattern of banding on gel electrophoresis. The known Shantz process can be used to obtain crystalline *botulinum* toxin type A, as set forth in Shantz, E. J., et al, *Properties and use of Botulinum toxin and Other Microbial Neurotoxins in Medicine*, Microbiol Rev. 56;80–99:1992. Generally, the *botulinum* toxin type A complex can be isolated and purified from an anaerobic fermentation by cultivating *Clostridium botulinum* type A in a suitable medium. The known process can also be used, upon separation out of the non-toxin proteins, to obtain pure *botulinum* toxins, such as for example: purified *botulinum* toxin type A with an approximately 150 kD molecular weight with a specific potency of $1-2 \times 10^8$ LD50 U/mg or greater; purified *botulinum* toxin type B with an approximately 156 kD molecular weight with a specific potency of $1-2 \times 10^8$ LD50 U/mg or greater, and; purified *botulinum* toxin type F with an approximately 155 kD molecular weight with a specific potency of $1-2 \times 10^7$ LD50 U/mg or greater.

*Botulinum* toxins and/or *botulinum* toxin complexes can be obtained from List Biological Laboratories, Inc., Campbell, Calif.; the Centre for Applied Microbiology and Research, Porton Down, U.K.; Wako (Osaka, Japan), Metabiologics (Madison, Wis.) as well as from Sigma Chemicals of St Louis, Mo. Pure *botulinum* toxin can also be used to prepare a pharmaceutical composition.

As with enzymes generally, the biological activities of the *botulinum* toxins (which are intracellular peptidases) is dependant, at least in part, upon their three dimensional conformation. Thus, *botulinum* toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin can stabilized with a stabilizing agent such as albumin and gelatin.

A commercially available *botulinum* toxin containing pharmaceutical composition is sold under the trademark BOTOX® (available from Allergan, Inc., of Irvine, Calif.). BOTOX® (a *botulinum* toxin type A complex) consists of a purified *botulinum* toxin type A complex, albumin and sodium chloride packaged in sterile, vacuum-dried form. The *botulinum* toxin type A is made from a culture of the Hall strain of *Clostridium botulinum* grown in a medium containing N-Z amine and yeast extract. The *botulinum* toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5° C. BOTOX® (a *botulinum* toxin type A complex) can be reconstituted with sterile, non-preserved saline prior to intramuscular injection. Each vial of BOTOX® (a *botulinum* toxin type A complex) contains about 100 units (U) of *Clostridium botulinum* toxin type A purified neurotoxin complex, 0.5 milligrams of human serum albumin and 0.9 milligrams of sodium chloride in a sterile, vacuum-dried form without a preservative.

To reconstitute vacuum-dried BOTOX® (a *botulinum* toxin type A complex), sterile normal saline without a preservative; (0.9% Sodium Chloride Injection) is used by drawing up the proper amount of diluent in the appropriate size syringe. Since BOTOX® (a *botulinum* toxin type A complex) may be dispersed or denatured by bubbling or similar violent agitation, the diluent is gently injected into the vial. For sterility reasons BOTOX® (a *botulinum* toxin type A complex) is preferably administered within four hours after the vial is removed from the freezer and reconstituted. During these four hours, reconstituted BOTOX® (a *botulinum* toxin type A comniex) can be stored in a refrigerator at about 2° C. to about 8° C. Reconstituted, refrigerated BOTOX® (a *botulinum* toxin type A complex) has been reported to retain its potency for at least about two weeks. *Neurology*, 48:249–53:1997.

It has been reported that *botulinum* toxin type A has been used in clinical settings as follows:

(1) about 75–125 units of BOTOX® (a *botulinum* toxin type A complex) per intramuscular injection (multiple muscles) to treat cervical dystonia;

(2) 5–10 units of BOTOX® (a *botulinum* toxin type A comniex) per intramuscular injection to treat glabellar lines (brow furrows) (5 units injected intramuscularly into the procerus muscle and 10 units injected intramuscularly into each corrugator supercilii muscle);

(3) about 30–80 units of BOTOX® (a *botulinum* toxin woe A complex) to treat constipation by intrasphincter injection of the puborectalis muscle;

(4) about 1–5 units per muscle of intramuscularly injected BOTOX® (a *botulinum* toxin type A complex) to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1–5 units of BOTOX® (a *botulinum* toxin type A complex), the amount injected varying based upon both the size of the muscle to be injected and the extent of muscle paralysis desired (i.e. amount of diopter correction desired).

(6) to treat upper limb spasticity following stroke by intramuscular injections of BOTOX® (a *botulinum* toxin type A complex) into five different upper limb flexor muscles, as follows:
(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachii: 50 U to 200 U. Each of the five indicated muscles has been injected at the same treatment session, so thai the patient receives from 90 U to 360 U of upper limb flexor muscle BOTOX® (a *botulinum* toxin type A complex) by intramuscular injection at each treatment session.

(7) to treat migraine, pericranial injected (injected symmetrically into glabellar, frontalis and temporalis muscles) injection of 25 U of BOTOX® (a *botulinum* toxin type A complex) has showed significant benefit as a prophylactic treatment of migraine compared to vehicle as measured by decreased measures of migraine frequency, maximal severity, associated vomiting and acute medication use over the three month period following the 25 U injection.

It is known that *botulinum* toxin type A can have an efficacy for up to 12 months (*European J. Neurology* 6 (Supp 4): S111–S1150:1999), and in some circumstances for as long as 27 months, when used to treat glands, such as in the treatment of hyperhydrosis. See e.g. Bushara K., *Botulinum toxin and rhinorrhea*, Otolaryngol Head Neck Surg 1996; 114(3):507, and *The Laryngoscope* 109:1344–1346:1999. However, the usual duration of an intramuscular injection of BOTOX® (a *botulinum* toxin type A complex) is typically about 3 to 4 months.

The success of *botulinum* toxin type A to treat a variety of clinical conditions has led to interest in other *botulinum* toxin serotypes. Two commercially available *botulinum* type A preparations for use in humans are BOTOX® (a *botulinum* toxin type A complex) available from Allergan, Inc., of Irvine, Calif., and DYSPORT® (a *botulinum* toxin A complex) available from Beaufour Ipsen, Porton Down, England. A *Botulinum* toxin type B preparation (MYOBLOC®) is available from Elan Pharmaceuticals of San Francisco, Calif.

U.S. Pat. No. 5,989,545 discloses that a modified Clostridial neurotoxin or fragment thereof, preferably a *botulinum* toxin, chemically conjugated or recombinantly fused to a particular targeting moiety can be used to treat pain by administration of the agent to the spinal cord.

A *botulinum* toxin has also been proposed for or has been used to treat a number of ailments, including for example otitis media of the ear (U.S. Pat. No. 5,766,605), inner ear disorders (U.S. Pat. Nos. 6,265,379; 6,358,926), tension headache, (U.S. Pat. No. 6,458,365), migraine headache pain (U.S. Pat. No. 5,714,468), post-operative pain and visceral pain (U.S. Pat. No. 6,464,986), hair growth and hair retention (U.S. Pat. No. 6,299,893), psoriasis and dermatitis (U.S. Pat. No. 5,670,484), injured muscles (U.S. Pat. No. 6,423,319), various cancers (U.S. Pat. No. 6,139,845), smooth muscle disorders (U.S. Pat. No. 5,437,291 including vasospastic disorders and injecting a *botulinum* toxin into the smooth muscle of a blood vessel)), and neurogenic inflammation (U.S. Pat. No. 6,063,768). Controlled release toxin implants are known (see e.g. U.S. Pat. Nos. 6,306,423 and 6,312,708) as is transdermal *botulinum* toxin administration (U.S. patent application Ser. No. 10/194,805).

International patent application WO 03/084567 discusses use of a *botulinum* toxin to treat a cardiovascular disorder, and WO 01/10458 discusses use of a *botulinum* toxin to treat a cardiac muscle disorder. Resolution of fainting spells after hyperhydrosis treatment is discussed in Moro E., et al, *Suppression of syncopes after botulinum toxin treatment*, Mov Disord 2002;17(Suppl 5):S242 ABS P780, and a reduction of facial flushing is discussed in Tugnoli V., et al., *The role of gustatory flushing in Frey's syndrome and its treatment with botulinum toxin type A*, Clin Auton Res 2002;12 (3):174–178.

Tetanus toxin, as well as derivatives (i.e. with a non-native targeting moiety), fragments, hybrids and chimeras thereof can also have therapeutic utility. The tetanus toxin bears many similarities to the *botulinum* toxins. Thus, both the tetanus toxin and the *botulinum* toxins are polypeptides made by closely related species of Clostridium (*Clostridium tetani* and *Clostridium botulinum*, respectively). Additionally, both the tetanus toxin and the *botulinum* toxins are dichain proteins composed of a light chain (molecular weight about 50 kD) covalently bound by a single disulfide bond to a heavy chain (molecular weight about 100 kD). Hence, the molecular weight of tetanus toxin and of each of the seven *botulinum* toxins (non-complexed) is about 150 kD.

Furthermore, for both the tetanus toxin and the *botulinum* toxins, the light chain bears the domain which exhibits intracellular biological (protease) activity, while the heavy chain comprises the receptor binding (immunogenic) and cell membrane translocational domains.

Further, both the tetanus toxin and the *botulinum* toxins exhibit a high, specific affinity for gangliocide receptors on the surface of presynaptic cholinergic neurons. Receptor mediated endocytosis of tetanus toxin by peripheral cholinergic neurons results in retrograde axonal transport, blocking of the release of inhibitory neurotransmitters from central synapses and a spastic paralysis. Contrarily, receptor mediated endocytosis of *botulinum* toxin by peripheral cholinergic neurons results has not been demonstrated to exhibit retrograde transport, but has the property of inhibition of acetylcholine exocytosis from the intoxicated peripheral motor neurons and a flaccid paralysis.

Finally, the tetanus toxin and the *botulinum* toxins resemble each other in both biosynthesis and molecular architecture. Thus, there is an overall 34% identity between the protein sequences of tetanus toxin and *botulinum* toxin type A, and a sequence identity as high as 62% for some functional domains. Binz T. et al., *The Complete Sequence of Botulinum Neurotoxin Type A and Comparison with Other Clostridial Neurotoxins*, J Biological Chemistry 265(16); 9153–9158:1990.

Acetylcholine

Typically only a single type of small molecule neurotransmitter is released by each type of neuron in the mammalian nervous system, although there is evidence which suggests that several neuromodulators can be released by the same neuron. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the bag 1 fibers of the muscle spindle fiber, by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secrete the neurotransmitter norepinephrine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic, neurons of the parasympathetic nervous system as well as in those stimulated by the postganglionic cholinergic neurons of the sympathetic nervous system. The nicotinic receptors are found in the adrenal medulla, as well as within the autonomic ganglia, that is on the cell surface of the postganglionic neuron at the synapse between the preganglionic and postganglionic neurons of both the sympathetic and parasympathetic systems. Nicotinic receptors are also found in many nonautonomic nerve endings, for example in the membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

What is needed therefore is a therapeutically effective method for treating a vascular disorder.

SUMMARY

The present invention meets this need and provides methods for treating vascular disorders. The methods include a step of administering an effective amount of a *botulinum* toxin directly to a blood vessel of a mammal to treat a vascular disorder. In one embodiment, treating the vascular disorder prevents an undesired constriction of a blood vessel.

The following definitions apply herein:

"About" means approximately or nearly and in the context of a numerical value or range set forth herein means ±10% of the numerical value or range recited or claimed.

"Alleviating" means a reduction in the occurrence of a vascular disorder symptom. Thus, alleviating includes some reduction, significant reduction, near total reduction, and total reduction of a vascular disorder symptom. An alleviating effect may not appear clinically for between 1 to 7 days after administration of a *botulinum* neurotoxin to a patient.

"*Botulinum* toxin" means a *botulinum* neurotoxin as either pure toxin (i.e. about 150 kDa weight molecule) or as a complex (i.e. about 300 to about 900 kDa weight complex comprising a neurotoxin molecule and one or more associated non-toxic molecules), and excludes *botulinum* toxins which are not neurotoxins such as the cytotoxic *botulinum* toxins C2 and C3, but includes recombinantly made, hybrid, modified, and chimeric *botulinum* toxins.

"Local administration" or "locally administering" means administration or making available (i.e. by a subcutaneous, intramuscular, subdermal or transdermal route) of a pharmaceutical agent to or to the vicinity of a dermal or subdermal location of a vascular disorder of a patient.

"Treating" means to alleviate (or to eliminate) at least one symptom of a vascular disorder, either temporarily or permanently.

"Vascular disorder" means an abnormal tone or abnormal constriction or dilation of a blood vessel. A vasomotor instability condition can be a vascular disorder due to an excessive dilatation, an excessive contraction, or abnormality in the contraction-relaxation process of a blood vessel, including in a region or complex of blood vessels. A vascular disorder can occur after a blood vessel graft or after tissue (i.e. kidney) transplant procedure.

A method within the scope of the present invention for treating a vascular disorder can have the step of local administration of a *botulinum* neurotoxin to a location of a vascular disorder of a patient, such as to a face, hand or foot of a patient. By local administration it is meant that the *botulinum* neurotoxin is administered, as by injection, directly to, in, or to the vicinity of, a region of a vascular disorder.

In the practice of our invention a *botulinum* neurotoxin can be locally administered in an amount of between about $10^{-3}$ units/kg of patient weight and about 35 units/kg of patient weight. Preferably, the neurotoxin is locally administered in an amount of between about $10^{-2}$ U/kg and about 25 U/kg of patient weight. More preferably, the neurotoxin is administered in an amount of between about $10^{-1}$ U/kg and about 15 U/kg. In a particularly preferred method within the scope of the present invention, the *botulinum* neurotoxin is locally administered in an amount of between about 1 U/kg and about 10 U/kg. In a clinical setting it can be advantageous to inject from 1 U to 3000 U of a neurotoxin, such as *botulinum* toxin type A or B, to a vascular disorder location by topical application or by subdermal administration, to effectively treat the vascular disorder.

A method according to my invention can be carried out by administration of a botulinum toxin to a patient with, or who is predisposed to, a vascular disorder. The botulinum toxin used is preferably a botulinum toxin (as either a complex or as a pure [i.e. about 150 kDa molecule], such as a botulinum toxin A, B, C, D, E, F or G. Administration of the botulinum toxin can be by a transdermal route (i.e. by application of a botulinum toxin in a cream, patch or lotion vehicle), subdermal route (i.e. subcutaneous or intramuscular) or intradermal route of administration or by injection of the botulinum toxin into a blood vessel wall.

The dose of a botulinum toxin used according to the present invention can be less than the amount of toxin that would be used to paralyze a muscle, since the intent of a method according to the present invention is not to paralyze a muscle but to treat a vascular disorder.

The botulinum neurotoxin is administered in a therapeutically effective amount to alleviate a symptom of a vascular disorder. A suitable botulinum neurotoxin may be a neurotoxin made by a bacterium, for example, the neurotoxin may be made from a Clostridium botulinum, Clostridium butyricum, or Clostridium beratti. In certain embodiments of the invention, the vascular disorder can be treated by applying to (topical) or into the wall of a blood vessel of a patient a botulinum toxin. The botulinum toxin can be a botulinum toxin type A, B, C1, D, E, F, or G. The vascular disorder alleviating effects of the botulinum toxin may persist for between about 2 weeks (i.e. upon administration of a short acting botulinum toxin, such as a botulinum toxin type E) and 5 years (i.e. upon implantation of a controlled release botulinum toxin implant). The botulinum neurotoxin can be a recombinantly made botulinum neurotoxin, such as a botulinum toxin produced by an E. coli bacterium. In addition or alternatively, the botulinum neurotoxin can be a modified neurotoxin, that is a botulinum neurotoxin which has at least one of its amino acids deleted, modified or replaced, as compared to a native or the modified botulinum neurotoxin can be a recombinant produced botulinum neurotoxin or a derivative or fragment thereof.

A method for treating a vascular disorder according to the present invention can comprise the step of local administration of a botulinum toxin to a patient with a vascular disorder to thereby alleviate the vascular disorder. The botulinum toxin can be selected from the group consisting of botulinum toxin types A, B, C, D, E, F and G. Botulinum toxin type A is a preferred botulinum toxin.

A detailed embodiment of my invention can comprise a method for treating a vascular disorder by local administration to a patient with a vascular disorder of between about 1 unit and about 3,000 units of a botulinum toxin (for example between about 1–50 units of a botulinum toxin type A or between about 50 to 3,000 units of a botulinum toxin type B), thereby alleviating the vascular disorder for between about two weeks and about 5 years.

My invention also encompasses a method for treating a vascular disorder by locally administering a botulinum toxin (such as a botulinum toxin type A, B, C, D, E, F or G, in an amount of from 1 unit to 3,000 units per treatment session) to a patient predisposed to experience vascular disorder, thereby preventing the patient from experiencing a vascular disorder. A patient predisposed to vascular disorder is a human who has experienced vascular disorder at least once within the last twelve months. The local administration can be carried out by subcutaneous or by topical administration of the botulinum toxin a location on or within a blood vessel of a patient where a vascular disorder is located.

DESCRIPTION

The present invention is based upon the discovery that a vascular disorder can be treated by local administration of a therapeutically effective amount of a botulinum neurotoxin. The botulinum neurotoxin (such as a botulinum neurotoxin serotype A, B, $C_1$ D, E, F or G) can be injected into or topically applied onto or in the vicinity of a vascular disorder of a patient. Alternately, the botulinum toxin can be administered to an intradermal or subdermal neuron to thereby downregulate, inhibit or suppress a neuronally mediated or influenced vascular disorder.

The methods disclosed herein are applicable to any blood vessel in the body including, but not limited to, coronary (heart), cerebral (brain), carotid (neck), renal (kidney), visceral (abdominal), lliac (hip), femoropopliteal (thigh), and infrapopliteal (knee) blood vessels. Our invention can be practised by local application of a botulinum toxin to a blood vessel of a patient experiencing or prone to experiencing a vasomotor instability. Local application means administration directly to the wall of a blood vessel which is a cause of the vasomotor instability or to the immediate vicinity of the target blood vessel (i.e. where the target blood vessels are a number of capillaries). A target blood vessel is one which shows a blood vessel contraction or dilation to such an extent as to produce an undesirable result in the patient (e.g. a spastic blood vessel).

Without wishing to be bound by theory a physiological mechanism can be proposed for the efficacy of my invention as disclosed herein for the treatment of a vascular disorder using a botulinum neurotoxin. Essentially, it is hypothesized that use of a botulinum toxin can inhibit release of acetylcholine and/or of another neurotransmitter or neuropeptide by one or more dermal or subdermal nerves or structures which innervate or which influence a vascular disorder, to thereby permit effective treatment of a vascular disorder. Alternately, the administered botulinum neurotoxin can have a direct effect upon a blood vessel affected by a vascular disorder. By effective treatment it is meant that the a more normal blood is achieved through the blood vessel afflicted by the vascular disorder.

The amount of a botulinum toxin administered according to a method within the scope of the disclosed invention can vary according to the particular characteristics of the vascular disorder being treated, including its severity and other various patient variables including size, weight, age, and responsiveness to therapy. To guide the practitioner, typically, no less than about 1 unit and no more than about 50 units of a botulinum toxin type A (such as BOTOX®, a botulinum toxin type A complex) is administered per injection site (i.e. to each vascular disorder location injected), per patient treatment session. For a botulinum toxin type A such as DYSPORT® (a botulinum toxin type A complex), no less than about 2 units and no more about 200 units of the botulinum toxin type A are administered per administration or injection site, per patent treatment session. For a botulinum toxin type B such as MYOBLOC® (a botulinum toxin type B preparation), no less than about 40 units and no more than about 2500 units of the botulinum toxin type B are administered per administer or injection site, per patient treatment session. Less than about 1, 2 or 40 units (of BOTOX® (a botulinum toxin type A complex), DYSPORT® (a botulinum toxin type A complex) and MYOBLOC® (a botulinum toxin type B preparation) respectively)

can fail to achieve a desired therapeutic effect, while more than about 50, 200 or 2500 units (of BOTOX® (a *botulinum* toxin type A complex) DYSPORT® (a *botulinum* toxin type A complex) and MYOBLOC® (a *botulinum* toxin type B preparation ) respectively) can result in clinically observable and undesired muscle hypotonicity, weakness and/or paralysis.

More preferably: for BOTOX® (a *botulinum* toxin type A complex) no less than about 2 units and no more about 20 units of a *botulinum* toxin type A; for DYSPORT® (a *botulinum* toxin type A complex) no less than about 4 units and no more than about 100 units, and; for MYOBLOC® (a *botulinum* toxin type B preparation), no less than about 80 units and no more than about 1000 units are, respectively, administered per injection site, per patient treatment session.

Most preferably: for BOTOX® (a *botulinum* toxin type A complex) no less than about 5 units and no more about 15 units of a *botulinum* toxin type A; for DYSPORT® (a *botulinum* toxin type A complex) no less than about 20 units and no more than about 75 units, and; for MYOBLOC® (a *botulinum* toxin type B preparation), no less than about 200 units and no more than about 750 units are, respectively, administered per injection site, per patient treatment session. It is important to note that there can be multiple injection sites (i.e. a pattern of injections) for each patient treatment session.

Although examples of routes of administration and dosages are provided, the appropriate route of administration and dosage are generally determined on a case by case basis by the health care provider, typically the attending physician. Such determinations are routine to one of ordinary skill in the art (see for example, *Harrison's Principles of Internal Medicine* (1998), edited by Anthony Fauci et al., 14th edition, published by McGraw Hill). For example, the route and dosage for administration of a *botulinum* neurotoxin according to the present disclosed invention can be selected based upon criteria such as the solubility characteristics of the neurotoxin chosen as well as the intensity and scope of a vascular disorder.

The present invention is based on the discovery that local administration of a *botulinum* neurotoxin can provide significant and long lasting relief from a vascular disorder. The *botulinum* neurotoxins are not cytotoxic to the cells exposed to the *botulinum* neurotoxin. The vascular disorder alleviation effect provided by the *botulinum* toxin can persist for a relatively long period of time, for example, for more than two months, and potentially for several years.

In one embodiment of the invention, the *botulinum* neurotoxin administered to the patient is *botulinum* toxin type A. *Botulinum* toxin type A is desirable due to its high potency in humans, ready availability, and known use for the treatment of skeletal and smooth muscle disorders when locally administered by intramuscular injection. The present invention also includes the use of (a) *botulinum* neurotoxins obtained or processed by bacterial culturing, toxin extraction, concentration, preservation, freeze drying, and/or reconstitution; and/or (b) modified or recombinant neurotoxins, that is neurotoxins that have had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made. These neurotoxin variants retain the ability to inhibit neurotransmission between or among neurons or other associated structures, and some of these variants may provide increased durations of inhibitory effects as compared to native neurotoxins, or may provide enhanced binding specificity to the neurons exposed to the neurotoxins. These neurotoxin variants may be selected by screening the variants using conventional assays to identify neurotoxins that have the desired physiological effects of inhibiting neurotransmission.

*Botulinum* toxins for use according to the present invention can be stored in lyophilized, vacuum dried form in containers under vacuum pressure or as stable liquids. Prior to lyophilization the *botulinum* toxin can be combined with pharmaceutically acceptable excipients, stabilizers and/or carriers, such as albumin. The lyophilized material can be reconstituted with saline or water to create a solution or composition containing the *botulinum* toxin to be administered to the patient.

Although the composition can contain a *botulinum* neurotoxin, such as *botulinum* toxin type A, as the active ingredient, other therapeutic compositions may include two or more types of neurotoxins, which may provide enhanced therapeutic treatment of a vascular disorder. For example, a composition administered to a patient may include *botulinum* toxin type A and *botulinum* toxin type B. Administering a single composition containing two different *botulinum* neurotoxins can permit the effective concentration of each of the neurotoxins to be lower than if a single neurotoxin is administered to the patient while still achieving the desired therapeutic effects. The composition administered to the patient may also contain other pharmaceutically active ingredients, such as, protein receptor or ion channel modulators, in combination with the neurotoxin or neurotoxins. These modulators may contribute to the reduction in neurotransmission between the various neurons.

The *botulinum* neurotoxin can be administered by any suitable method as determined by the attending physician. The methods of administration permit the neurotoxin to be administered locally to a selected target tissue. Methods of administration include injection of a solution or composition containing the neurotoxin, as described above, and include implantation of a controlled release system that controllably releases the neurotoxin to the target tissue. Such controlled release systems reduce the need for repeat injections. Diffusion of biological activity of a *botulinum* toxin within a tissue appears to be a function of dose and can be graduated. Jankovic J., et al *Therapy With Botulinum Toxin*, Marcel Dekker, Inc., (1994), page 150. Thus, diffusion of *botulinum* toxin can be controlled to reduce potentially undesirable side effects that may affect the patient's cognitive abilities. For example, the neurotoxin can be administered so that the neurotoxin primarily effects neural systems believed to be involved in the generation of a vascular disorder.

Local administration of a *botulinum* toxin, such as a *botulinum* toxin, can provide a high, local therapeutic level of the toxin. A controlled release polymer capable of long term, local delivery of a *botulinum* toxin to a target vascular disorder location permits effective dosing of the target tissue. A suitable implant, as set forth in U.S. Pat. No. 6,306,423 entitled "Neurotoxin Implant", allows the direct introduction of a *botulinum* toxin to a target tissue via a controlled release polymer.

Local administration of a *botulinum* toxin, according to the present invention, by injection or implant to a target tissue provides a superior alternative to systemic administration of pharmaceuticals to patients to alleviate a vascular disorder.

The amount of a *botulinum* toxin selected for local administration to a target tissue according to the present disclosed invention can be varied based upon criteria such as the severity of the vascular disorder being treated, solubility characteristics of the neurotoxin toxin chosen as well as the age, sex, weight and health of the patient. For example, the extent of the area of vascular disorder influenced is believed to be proportional to the volume of neurotoxin injected, while the quantity of the vascular disorder suppressant effect is, for most dose ranges, believed to be proportional to the concentration of a *botulinum* toxin administered. Methods for determining the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., 14th edition, published by McGraw Hill).

Significantly, a method within the scope of the present invention can provide improved patient function. "Improved patient function" can be defined as an improvement measured by factors such as a reduced pain, reduced time spent in bed, increased ambulation, healthier attitude, more varied lifestyle and/or healing permitted by normal muscle tone. Improved patient function is synonymous with an improved quality of life (QOL). QOL can be assessed using, for example, the known SF-12 or SF-36 health survey scoring procedures. SF-36 assesses a patient's physical and mental health in the eight domains of physical functioning, role limitations due to physical problems, social functioning, bodily pain, general mental health, role limitations due to emotional problems, vitality, and general health perceptions. Scores obtained can be compared to published values available for various general and patient populations.

EXAMPLES

The following non-limiting examples provide those of ordinary skill in the art with specific preferred methods to treat conditions within the scope of the present invention and are not intended to limit the scope of the invention. In the following examples various modes of non-systemic administration of a *botulinum* neurotoxin can be carried out. For example, by topical application (cream or transdermal patch), subcutaneous injection, injection into specific tissues, or by implantation of a controlled release implant.

Example 1

Use of Botulinum Toxin in Conjunction with a Kidney Transplant

A patient receives a kidney transplant. Prior to or concurrently with the kidney transplant, 1 to 50 unit of a *botulinum* toxin type A is injected into the wall of the renal artery in proximity to the transplanted kidney in order to prevent the constriction of the renal artery after the transplant. The patient thereby exhibits normal blood flow through the renal artery after the transplant.

Example 2

Use of Botulinum Toxin to Treat Raynaud's Syndrome

A female patient age 26 presents with a diagnosis of Raynaud's syndrome. The skin of her fingers and toes exhibits a patchy red color. A total of 100 units of a *botulinum* toxin is injected subdermally (5 units into each of her 20 digits) into each finger and toe. Within two week her symptoms regresses, her skin returns to a normal hue and she remains symptom free for 3 to 4 months.

Example 3

Use of Botulinum Toxin to Treat Vasospasms after Subarachnoidal Bleeding

A male patient age 55 experiences sudden headache after subarachnoidal bleeding from a ruptured aneurysm of the left middle cerebral artery. Because of a symptomatic hydrocephalus, a ventricle drainage via catheter can be performed. Three days after the bleeding he develops a mild hemiparesis and transcranial Doppler sonography identifies vasospasms of both middle and anterior cerebral arteries. Intrathecal administration of *botulinum* toxin type B via the ventricle catheter leads to a marked reduction of vasospasms within 48 hours as the Doppler sonography shows. MRI does not show any ischemic lesion of the brain. He completely recovers without any neurological deficits.

Example 4

Use of a Botulinum Toxin to Improve Blood Supply through a Graft

A patient 67 undergoes preparation for a coronary artery bypass graft (CABG). The patient develops atherosclerosis in his coronary arteries, the flow of blood through these vessels is blocked, and the blood supply to heart muscle is jeopardized. Prognosis is a heart attack or sudden death. The CABG operation is designed to re-route the blood around these blockages to prevent a heart attack or sudden death. Conventionally, with this patient an artery from behind the breast bone, and veins from the legs is used to bypass the blood around the coronary artery blockages.

The operation takes 2–3 hours to perform, and begins after general anesthesia is induced. The patient is completely asleep during the entire course of the operation. A physician assistant remove saphenous vein through incisions in the legs. The length of the incision is dependent upon the amount of vein required to complete the necessary number of bypasses. There are many redundant veins in the patient's leg. Once some vein is removed, the other veins in the leg take over for the missing vein. Once the vein has been removed from the leg, it has the appearance of a long tube or conduit. The vein is divided into separate shorter segments, each of which can be used for individual bypasses. Into the arterial wall of each segment which will be used as a bypass graft five units of a *botulinum* toxin type A is injected.

As vein is removed from the leg by a physician assistant, the surgeon simultaneously opens the chest by dividing the breast bone or sternum, affording excellent exposure of the heart. An artery behind the sternum, the left internal mammary artery (LIMA) is taken down and one end prepared for bypass grafting. Tubes or cannulae are inserted into the heart and major blood vessels surrounding the heart in preparation for cardiopulmonary bypass with the heart-lung machine.

At this point, the patient is placed on the heart-lung machine. Blood is re-directed from the heart into the heart-lung machine. This permits the surgeon to safely operate on the heart without blood pumping through it. The heart is then stopped, and the heart-lung machine continues to pump freshly oxygenated blood to the rest of the body, in effect, taking over the roles of the heart and lungs.

The diseased coronary arteries are now identified and opened beyond the level of the blockages. The open ends of the saphenous veins and LIMA are now sewn to the openings in the coronary arteries using very fine non-absorbable suture material, called the distal anastamoses. The surgeon wears magnifying lenses in order to see the delicate suture and small vessels.

Because the inflow through the LIMA is left intact, as soon as the LIMA anastamosis is completed, blood flow is established to that region of the heart. A vein graft however, is harvested as a free graft and has no inflow. Therefore, after the distal vein graft anastamosis is constructed, the other end of the vein graft is sewn to the aorta (the main artery leaving the heart) in order to establish inflow. These are called the proximal anastamoses. After this stage, blood flow has now been established beyond all the blocked arteries, and the heart has effectively been bypassed.

The heart-lung machine is then gradually weaned off, and the patient's heart and lungs resume their normal functions. The cannulae are removed from in and around the heart, and the sternum and incisions are closed. Drainage catheters are placed around the heart. These are usually removed after 24 hours. Temporary pacing wires to regulate the patient's heart rate, are sewn to the surface of the heart. These are removed before the patient goes home.

The patient can awaken from anesthesia 4–6 hours after the operation. The following morning all drainage catheters and monitoring lines can be removed. The patient is hospitalized for 4–5 days following the surgery. Although stenosis of the graft and occlusion of blood flow through the graft is a common post-operative complication, with this patient the graft heals without inflammation or graft stenosis (no collapse of the graft) occurring due to the intra-operative injection of graft with the *botulinum* toxin.

Our invention also includes within its scope the use of a *botulinum* toxin, in the preparation of a medicament for the treatment of a vascular disorder. All references, articles, patents, applications and publications set forth above are incorporated herein by reference in their entireties.

Accordingly, the spirit and scope of the following claims should not be limited to the descriptions of the preferred embodiments set forth above.

We claim:

1. A method for improving blood supply through a grafted blood vessel, the method comprising the step of locally administering a *botulinum* toxin to the grafted blood vessel, thereby improving blood supply through the grafted blood vessel.

2. The method of claim 1 wherein the administering step includes the step of injecting the *botulinum* toxin into a wall of the grafted blood vessel.

3. The method of claim 1 wherein the *botulinum* toxin is selected from the group consisting of *botulinum* toxin types A, B, C, D, E, F and G.

4. The method of claim 1 wherein the *botulinum* toxin is a *botulinum* toxin type A.

5. A method for reducing inflammation at the site of a grafted blood vessel, the method comprising the step of locally administering a *botulinum* toxin to the grafted blood vessel, thereby reducing inflammation at the site of the grafted blood vessel.

6. A method for preventing graft stenosis of a grafted blood vessel, the method comprising the step of locally administering a *botulinum* toxin to the grafted blood vessel, thereby preventing graft stenosis of the grafted blood vessel.

7. The method of claim 5 or 6 wherein the administering step includes the step of injecting the *botulinum* toxin into a wall of the grafted blood vessel.

* * * * *